United States Patent
Jin et al.

(10) Patent No.: US 7,861,711 B2
(45) Date of Patent: Jan. 4, 2011

(54) METHOD FOR JUDGING THE REVERSE CONNECTION OF A FLOW SENSOR AND A RESPIRATORY MECHANICS MEASURING MODULE USED THEREIN

(75) Inventors: Wei Jin, Shenzhen (CN); Zhiwei Huang, Shenzhen (CN); Jilun Ye, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1032 days.

(21) Appl. No.: 11/636,220

(22) Filed: Dec. 8, 2006

(65) Prior Publication Data
US 2007/0181127 A1 Aug. 9, 2007

(30) Foreign Application Priority Data
Jan. 20, 2006 (CN) .................. 2006 1 0033205

(51) Int. Cl.
- A61B 5/08 (2006.01)
- A61M 16/00 (2006.01)
- A62B 9/00 (2006.01)
- A62B 27/00 (2006.01)
- G08B 3/00 (2006.01)
- G08B 5/00 (2006.01)

(52) U.S. Cl. .................. 128/202.22; 600/529

(58) Field of Classification Search ..............
128/205.27–205.29, 206.12–206.17, 204.21–204.23,
128/202.22; 600/529; 73/196; 340/540,
340/603–608, 611; 137/313–327, 557
See application file for complete search history.

(56) References Cited

U.S. PATENT DOCUMENTS

| | | | | |
|---|---|---|---|---|
| 4,883,051 A | * | 11/1989 | Westenskow et al. | .. 128/204.21 |
| 5,558,086 A | | 9/1996 | Smith et al. | |
| 5,969,600 A | * | 10/1999 | Tanguay | ...................... 340/438 |
| 6,946,827 B2 | * | 9/2005 | Rahmatian et al. | ............. 324/96 |
| 7,570,979 B2 | * | 8/2009 | Cooper | ......................... 600/323 |
| 2002/0029003 A1 | * | 3/2002 | Mace et al. | .................. 600/532 |
| 2006/0283450 A1 | * | 12/2006 | Shissler et al. | ......... 128/204.21 |

FOREIGN PATENT DOCUMENTS

| | | |
|---|---|---|
| CN | 1285038 A | 2/2001 |
| CN | 1668243 A | 9/2005 |
| JP | 200129616 A | 2/2001 |
| WO | WO 2004/084980 | 10/2004 |

* cited by examiner

*Primary Examiner*—Justine R Yu
*Assistant Examiner*—Kristen C Matter
(74) *Attorney, Agent, or Firm*—Kory D. Christensen; Stoel Rives LLP

(57) ABSTRACT

A respiratory mechanics measuring module includes a flow sensor, a differential-pressure sensor and a sampled-signal processing circuit which are connected in series. The module further includes a flow sensor reverse connection judging module and an alarm. The flow sensor reverse connection judging module judges the reverse connection of the flow sensor. The alarm gives an alarm signal indicating the flow sensor reverse connection to the main controller when the flow sensor reverse connection judging module judges that the flow sensor is reversedly connected.

9 Claims, 5 Drawing Sheets

METHOD FOR JUDGING THE REVERSE CONNECTION OF A FLOW SENSOR AND A RESPIRATORY MECHANICS MEASURING MODULE USED THEREIN

STATEMENT OF RELATED APPLICATION

The present application claims the priority of the Chinese Patent Application No. 200610033205.5, filed on Jan. 20, 2006, entitled "A Method for Judging the Reverse Connection of a Flow Sensor and a Respiratory Mechanics Measuring Module Used Therein", which is incorporated herein by reference in its entirety.

FIELD OF THE INVENTION

The present invention relates to an apparatus for measuring respiratory flow, more particularly to a respiratory mechanics measuring module and a method for judging the reverse connection (or transposition) of a flow sensor in this module.

BACKGROUND OF THE INVENTION

Flow sensors as accessories of the respiratory mechanics modules or the anesthetic machines are the key devices that deliver the information on the airway communicating between the patients and the anesthetic machines to the monitoring modules, and play an important role in monitoring the respiratory mechanics parameters and the working states of the anesthetic machines. The monitoring of the respiratory mechanics parameters during operations not only determines the accuracy and safety of the respiratory mechanics modules in monitoring the patients' pulmonary ventilation process, but also plays a decisive role in the ventilation modes and the performance that the anesthetic machines can achieve.

Current commercially-available patient monitoring systems or anesthetic machines having respiratory mechanics parameters monitoring functions have not been provided with the function for monitoring the installation states of the flow sensors, nor do any technical solutions or relevant patents give clues thereto. The most frequently used method is to make the external diameter of the air nozzle located at the sensor module end into different sizes in order to prevent blind insertion, or to apply different indicative colors for guiding the user on correct installation of the flow sensors. Though this kind of method woks to some extent, it is not sufficient to prevent a user without any engineering knowledge from erroneous operations. Moreover, this kind of connection is not adapted for connecting the gas tubing of the flow sensors available on the market.

In another kind of respiratory mechanics module a trapezoidal socket and a photo-coupled circuit are provided at the back end of the flow sensor, which can discern the types of flow sensors and prevent the reverse connection of the flow sensors. This module provides timely and reliable solutions, but unfortunately is compromised by a relatively high cost. Moreover it can not address the problem as to the reverse connection of the flow sensors at the patient end either.

SUMMARY OF THE INVENTION

It is an object of the present invention to provide a method for judging the reverse connection of a flow sensor and a respiratory mechanics measuring module used in the method.

The present invention achieves the above object with the following technical solution:

A method for judging the reverse connection of a flow sensor in respiratory mechanics measurement, which method comprises the steps of:

a. connecting the flow sensor to a respiratory mechanics measuring module;

b. sampling consecutively airway pressures and flows of a respiratory gas flowing between a patient and an anaesthetic machine;

c. judging that the flow sensor is reversedly connected and sending an alarm signal indicating the reverse connection of the flow sensor to a main controller when any one of the following two instances appears:

1) when the airway pressure decreases to the lowest point, the flow has a negative value while the patient is inhaling; and 2) around the time when the pressure intensity decreases the fastest, the flow has a positive value.

The first instance is applicable for autonomous respiration mode, while the second instance is applicable for mechanical ventilation mode.

The process of sampling consecutively the airway pressures and flows of a respiratory gas flowing between a patient and an anesthetic machine as stated in step b comprises the following steps of: collecting a time sequence of the pressure intensity $x1$, $x2$, $x3$ and $x4$ at four consecutive sampling points of time within an arbitrary time interval and the flow value S corresponding to that time interval as the basis for the following judgment, and calculating three pressure difference variables using the equations $dx1=x1-x2$, $dx2=x2-x3$ and $dx3=x3-x4$.

The two instances as stated in step c, the occurrence of which indicates the reverse connection of the flow sensor, are as follows:

1) $x1$, $x2$ and $x3$ are all smaller than zero and $x1$ and $x3$ are all equal to or greater than $x2$, and the flow value S is smaller than a predetermined first threshold value f1; and 2) $dx1$, $dx2$ and $dx3$ are all greater than zero and $dx1$ and $dx3$ are all smaller than or equal to $dx2$, and the flow value S is greater than a predetermined second threshold value f2.

The first threshold value f1 is set at −2 liters/minute and the second threshold value f2 is set at 3 liters/minute, both of which are useful for eliminating misjudgment caused by tiny and weak interference.

After the system receives the alarm signal indicating the reverse connection of the flow sensor, the operator will shut down the machine and connect and install the flow sensor again. If the system does not receive any alarm signal, it indicates that the flow sensor is correctly connected, so that the user can be rest assured to use the respiratory mechanics measuring module.

The present invention further provides a respiratory mechanics measuring module, which module comprises a flow sensor, a differential-pressure sensor and a sampled-signal processing circuit which are connected in series. The sampled-signal processing circuit is used to transfer the calculation results to a main controller.

The module further comprises a flow sensor reverse connection judging module and an alarm, wherein the flow sensor reverse connection judging module judges whether the flow sensor is reversedly connected based on the output signals of the differential pressure sensor, and the alarm sends a prompting signal indicating the flow sensor reverse connection to the main controller when the flow sensor reverse connection judging module judges that the flow sensor is reversedly connected.

The sampled-signal processing circuit comprises an amplification circuit connected to the signal output end of the differential-pressure sensor, an analog-to-digital converter, a gain controller and a single chip processor, which is in bi-directional communication with the analog-to-digital converter and the main controller, respectively.

The flow sensor reverse connection judging module is an algorithm program solidified in the single chip processor.

In comparison with the prior art, the method for judging the reverse connection of a flow sensor and the respiratory mechanics measuring module used in the method according to the present invention achieves great advantageous effect. Specifically, it significantly reduces the manufacturing costs of the respiratory mechanics measuring modules, and it is possible to recognize the reverse connection of a flow sensor at the patient end, leading to improved efficiency as well as reliability and safety of the respiratory mechanics measuring modules.

DESCRIPTION OF THE PREFERRED EMBODIMENTS

In the following, preferred embodiments of the respiratory mechanics measuring module and the method for judging the reverse connection of a flow sensor according to the present invention will be described in further details in combination with the accompanying drawings.

The basic parameters measured by the respiratory mechanics measuring module include the real-time pressure intensity and the real-time flow in the airway. This is how they are measured. The flow sensor senses the absolute pressure intensity (relative to the atmospheric pressure) of the airway and the difference of pressure intensity between two conduits, which difference is then used to scale the flow so as to measure the value of the flow indirectly. Other real-time parameters and parameters concerning the respiratory cycle are all calculated on the basis of these two parameters.

Figure 1:
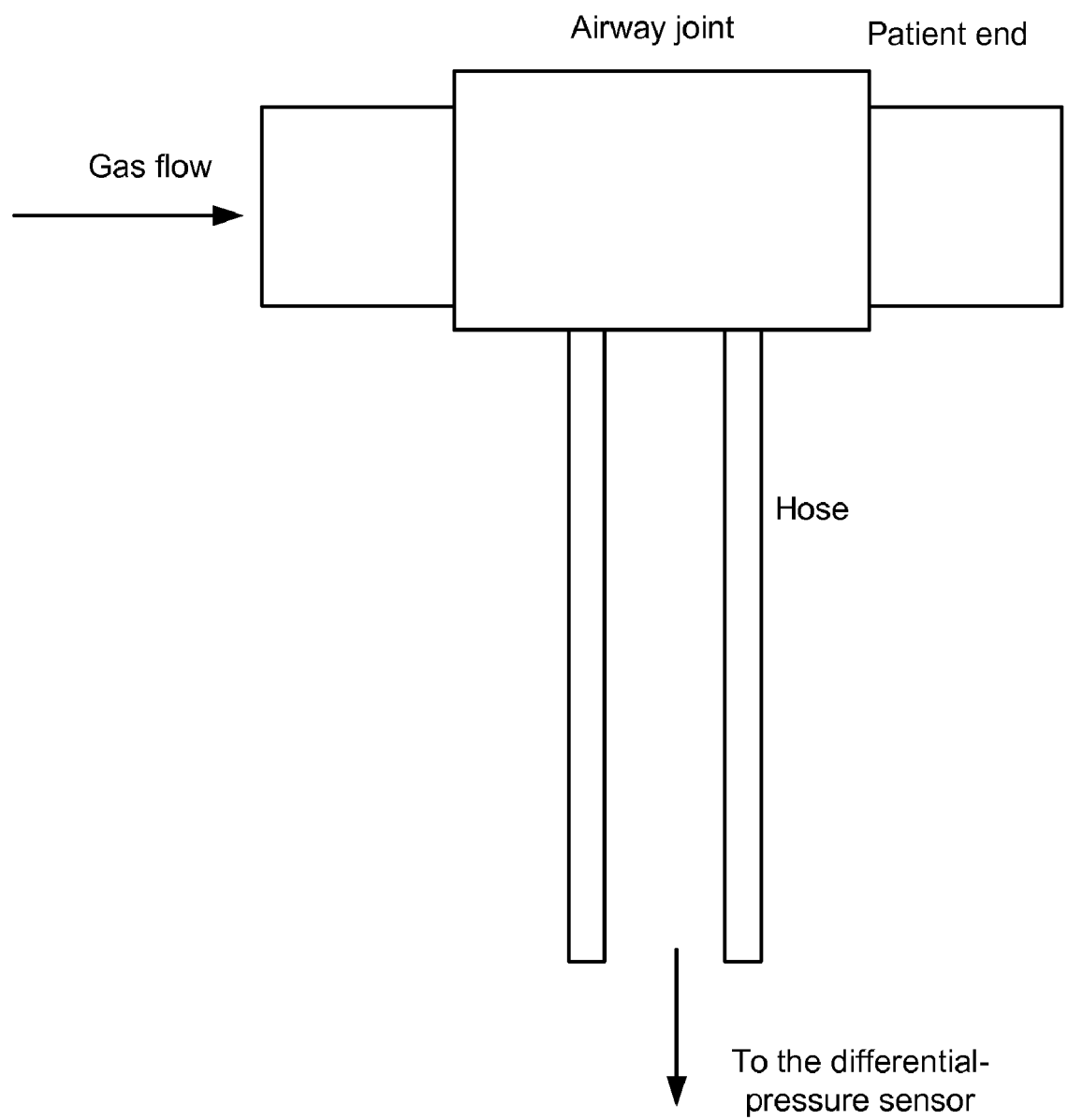
FIG. 1 is a structural schematic illustration of a flow sensor.

FIG. 1 is a structural schematic illustration of the flow sensor, in which the two hoses are to the sensor module end, while the right port of the airway joint is to the patient end. There are two instances of reverse connection of the flow sensor: one is a reverse connection at the patient end, the other is a reverse connection at the sensor module end. The reverse connection at the sensor module end means the two conduits of the sensor are transposed. To a user without too much engineering knowledge, this kind of transposition can hardly be avoided. The reverse connection at either end will result in incorrect measurement, which in turn leads to false diagnostic results.

Figure 2:
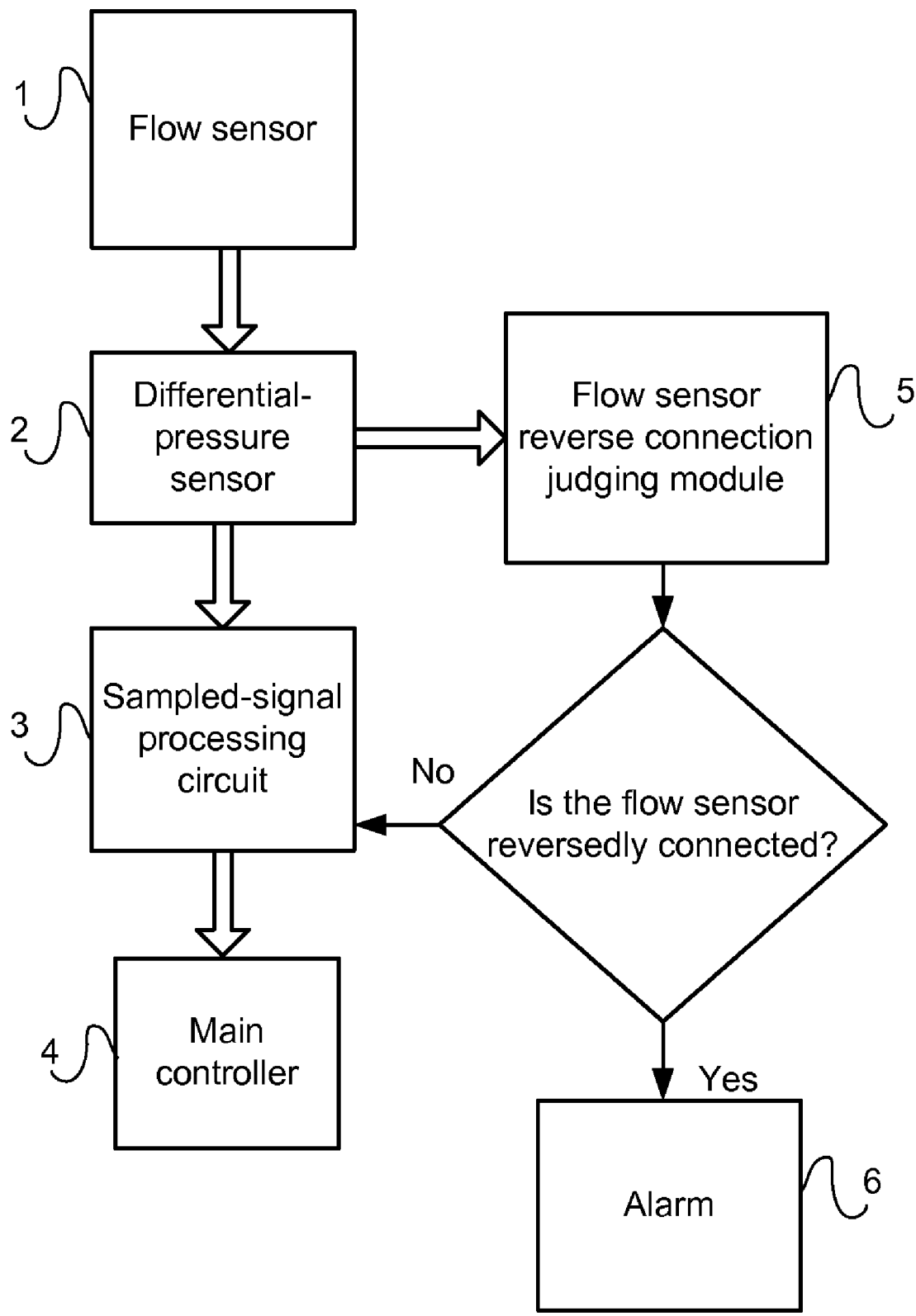
FIG. 2 is a first-level schematic diagram illustrating the structure of a respiratory mechanics module system according to the present invention.

As shown in FIG. 2, the respiratory mechanics measuring module according to the present invention comprises a flow sensor 1, a differential pressure sensor 2 and a sampled-signal processing circuit 3 which are connected in series. The module further comprises a flow sensor reverse connection judging module 5 and an alarm 6. The flow sensor reverse connection judging module 5 judges whether the flow sensor 1 is reversedly connected according to the output signals of the differential pressure sensor 2, and the alarm 6 sends a prompting signal indicating the reverse connection of the flow sensor to a main controller 4 (which is also referred to as a higher level controller) when the flow sensor reverse connection judging module 5 judges that the flow sensor is reversedly connected. The calculated results from the sampled-signal processing circuit 3 are output to the main controller 4.

Figure 3:
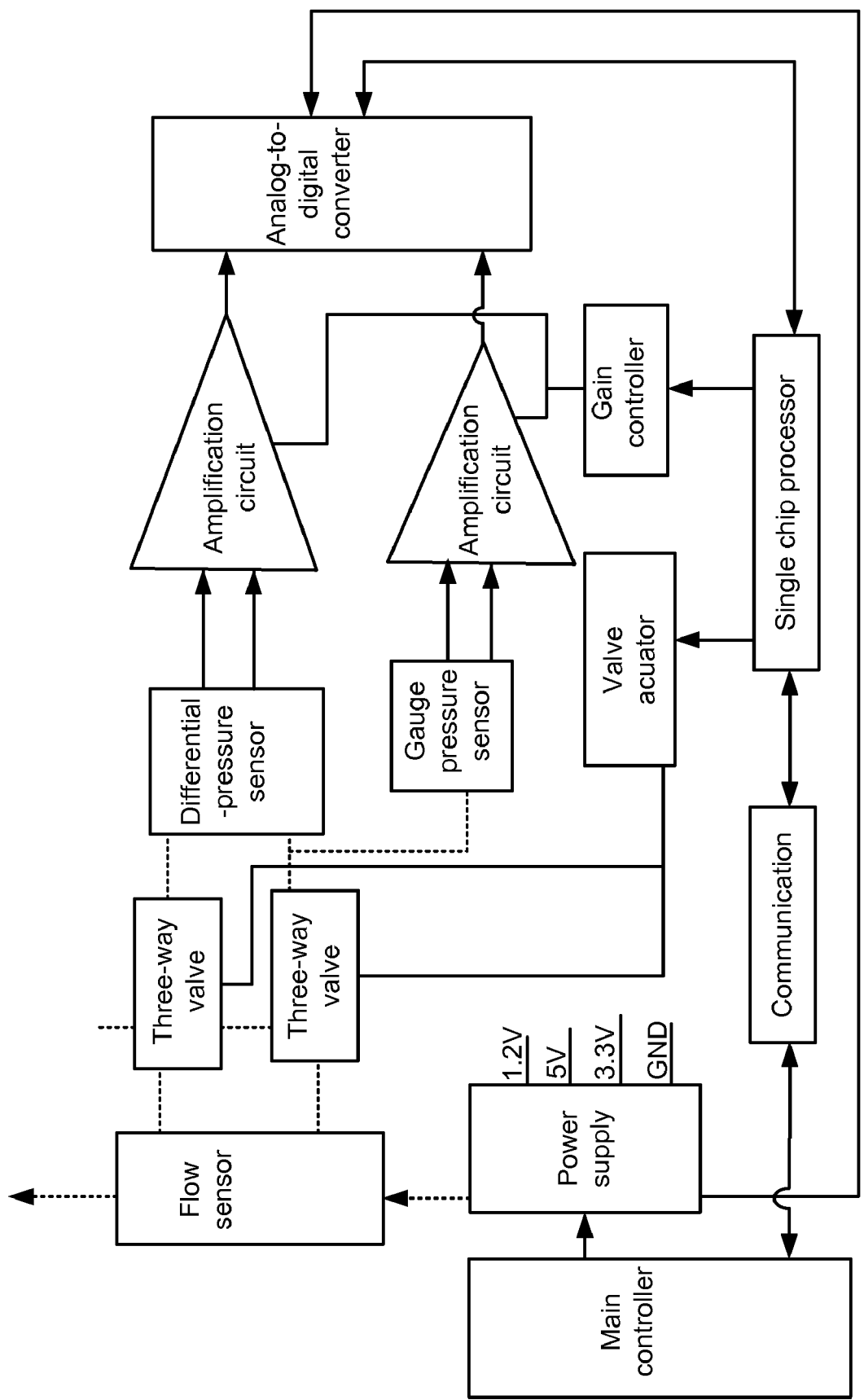
FIG. 3 is a second-level schematic diagram illustrating the structure of a respiratory mechanics module system according to the present invention.

FIG. 3 is a second-level schematic diagram illustrating the structure of a respiratory mechanics module system according to the present invention. As shown, the broken lines represent the connection of the airway and the arrows indicate the flow of the signal. The sampled-signal processing circuit 3 comprises an amplification circuit connected to the signal output end of the differential pressure sensor 2, an analog-to-digital converter, a gain controller and a single chip processor, the single chip processor being in bi-directional communication with the analog-to-digital converter and the main controller 4, respectively.

As shown in FIG. 3, two three-way valves connected to a valve actuator are provided between the flow sensor 1 and the differential-pressure sensor 2, one of which valves can also be connected to a gauge pressure sensor.

The flow sensor reverse connection judging module 5 is an algorithm program solidified in the single chip processor. Having been equipped with the above-described software and hardware facilities of the respiratory mechanics measuring module, it is possible to design a method for judging the reverse connection of a flow sensor by studying the measured parameters relating to respiratory mechanics.

The measurement in respiratory mechanics is divided into the measurement under an autonomous respiration state and the measurement under a mechanical ventilation state. As the pressure intensity and flow under respective state have different characteristics from each other, a judgment on the reverse connection of the flow sensor thereby will not be comprehensive until it is analyzed under the autonomous respiration state and the mechanical ventilation state, respectively.

Figure 4:
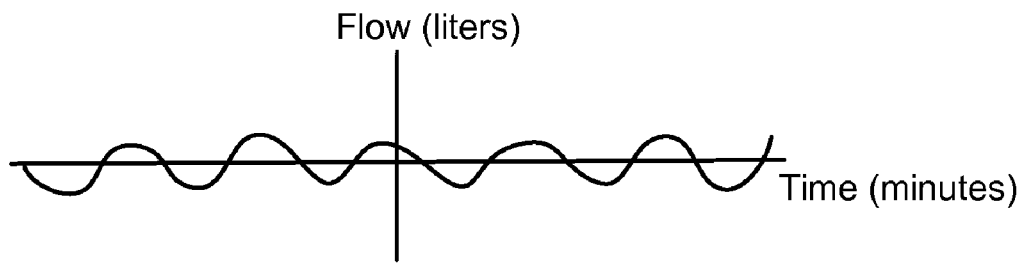
FIG. 4 is a schematic illustration of the normal waveforms of pressure intensity and flow under an autonomous respiration state.
Figure 4:
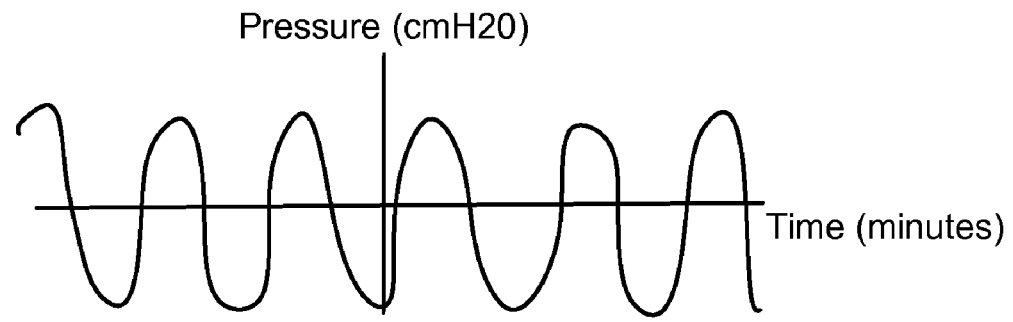
Figure 5:
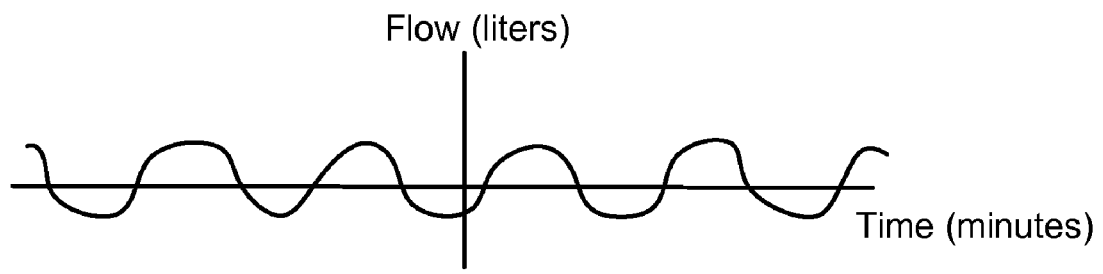
FIG. 5 is a schematic illustration of the waveforms of pressure intensity and flow under an autonomous respiration state where the flow sensor is reversedly connected.
Figure 5:
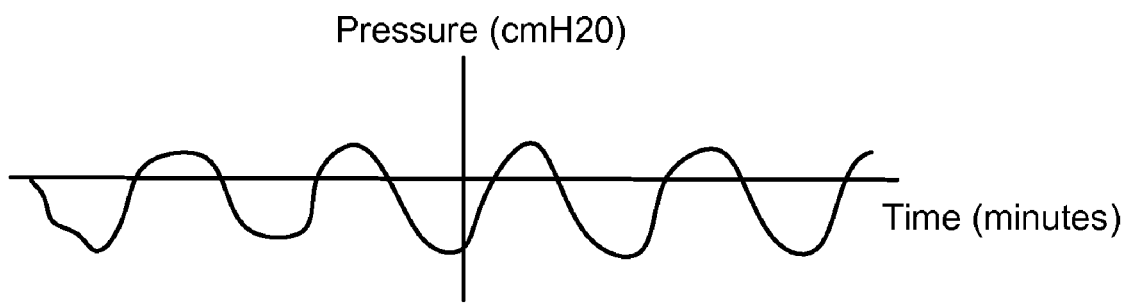

Under the autonomous respiration state, the characteristic waveforms of the airway pressure and flow are as shown in FIG. 4. In case of a steady breathing, the airway pressure and flow exhibit a roughly identical periodic variation. Whether the flow sensor 1 is connected obversely (that is in its normal position) or reversedly does not influence the positive and negative values of the airway pressure, but does influence the positive and negative direction of the flow velocity. In view of this characteristic, an inhalation must be being done when the airway pressure decreases to its lowest level. At that time, the flow value must be positive if the flow sensor is connected obversely, while the flow value is negative if the flow sensor is connected reversedly (as shown in FIG. 5). This happens because, when inhaling, the pressure intensity of the gas in the airway is greater than that in the patient's lungs but smaller than or equal to the atmosphere pressure, so that at that moment the gas must flow from the atmosphere into the patient's lungs through the tubing. This direction is generally defined as the positive direction in a respiratory mechanics module. Based on this law, a software algorithm can be set up in a sub-controller (which is also referred to as a lower level controller) applied in the respiratory mechanics measurement, comprising the following steps of:

a) upon recognition of the breathing waveform, recording the real-time pressure intensity x1, x2, and x3 respectively corresponding to three arbitrary consecutive sampling points and the flow value S corresponding to the middle between said sampling points;

b) examining the flow value S if x1, x2 and x3 are all smaller than zero and meanwhile x1 and x3 equal to or greater than x2;

c) sending an alarm signal for once to the main controller if the flow value S is smaller than a certain threshold value (referred to as the first threshold value f1), suggesting a reverse connection of the flow sensor. This first threshold value is set for eliminating false judgment due to tiny and weak interference, which may be, for example, −2 liters/minute.

It is also an alternative to, upon recognition of the breathing waveform, record the flow values and examine the value of the pressure intensity occurring when the flow value is at wave trough, so as to judge the existence of a reverse connection and then give an alarm.

Figure 6:
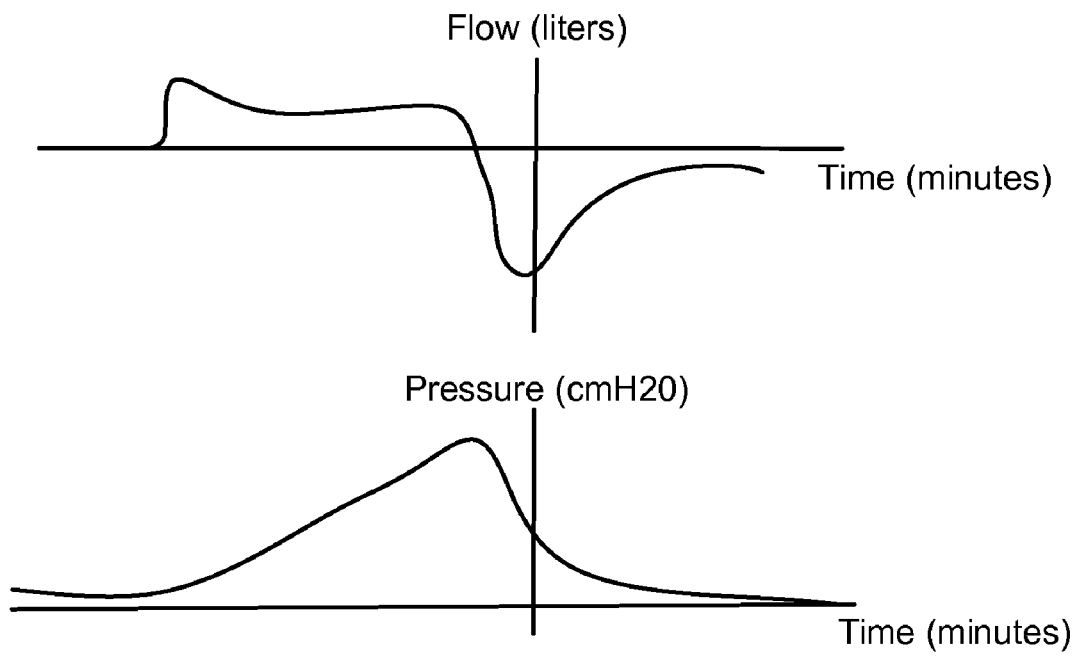
FIG. 6 is a schematic illustration of the normal waveforms of pressure intensity and flow under a mechanical ventilation state.

Under the mechanical ventilation state, breathing is effected with the pressure produced by mechanical devices, so it is a passive breathing that is carried out in the human lung organ (or test lungs). The characteristic waveforms of the airway pressure intensity and flow under a mechanical ventilation state are as shown in FIG. 6.

In case of a steady mechanical ventilation, the parameters concerned are characterized as that the values of the pressure intensity keep greater than zero, and that the values of the airway pressure intensity and flow exhibit an identical periodic variation. Upon continuous experiments and repeated research, it is observed that, with the flow sensor being correctly connected, the wave trough of the airway flow always appears at times when the airway pressure intensity decreases the most rapidly, as shown in FIG. 6.

Figure 7:
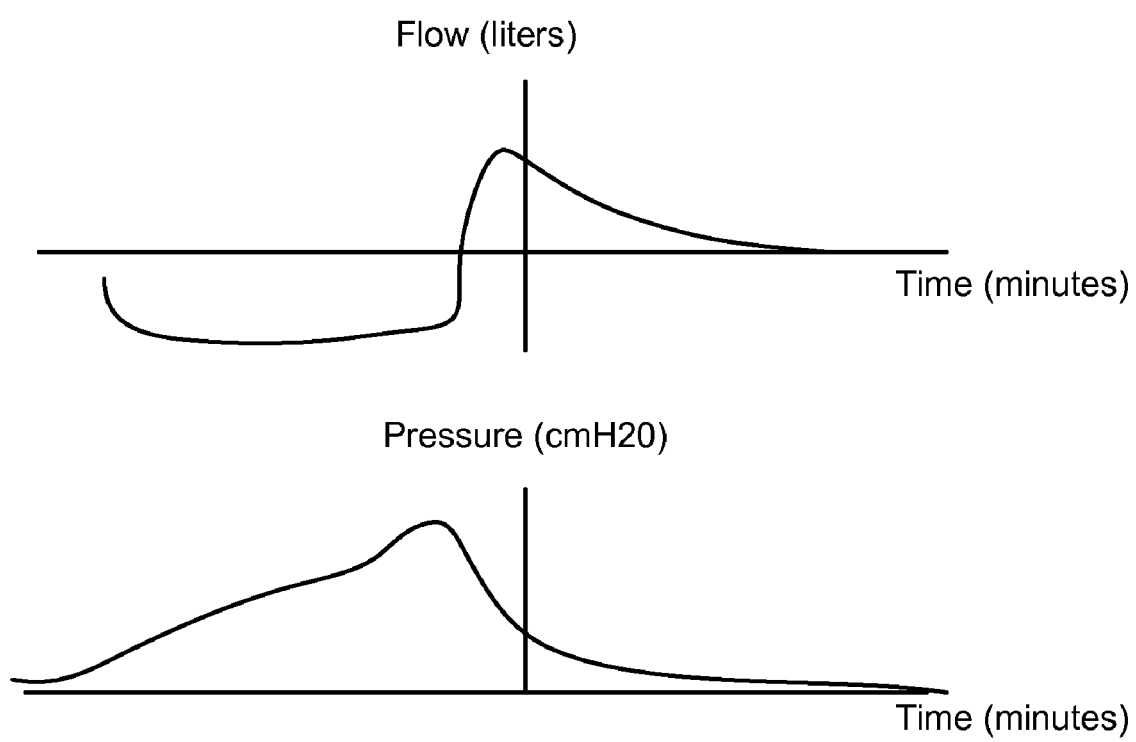
FIG. 7 is a schematic illustration of the waveforms of pressure intensity and flow under a mechanical ventilation state where the flow sensor is reversedly connected.

As already discussed above, whether the flow sensor is reversedly connected or not, the positive and negative values of the absolute pressure measured in the airway will not be influenced. In view of this, it can be easily deduced that the flow must have a positive value around times when the pressure intensity decreases the fastest, if the flow sensor is connected reversedly, as shown in FIG. 7. Based thereon, a software algorithm may be set up in the sub-controller, comprising the following steps of:

a) upon recognition of the breathing waveform, recording the real time pressure intensity x1, x2, x3 and x4 respectively corresponding to four consecutive sampling points;

b) calculating three pressure difference variables dx1, dx2 and dx3, which are defined as dx1=x1−x2, dx2=x2−x3 and dx3=x3−x4;

c) examining the flow value S if dx1, dx2 and dx3 are all greater than zero and meantime dx1 and dx3 are smaller than or equal to dx2, d) sending an alarm signal for once to the main controller if the flow value S is greater than a certain threshold value (referred to as the second threshold value f2), suggesting a reverse connection of the flow sensor. This second threshold value is also set for eliminating false judgment due to tiny and weak interference, which may be, for example, 3 liters/minute.

Based on the results of the above analysis, a method for judging the reverse connection of a flow sensor in respiratory mechanics measurement can be summed up, comprising the following steps of:

a. connecting the flow sensor to a respiratory mechanics measuring module;

b. sampling consecutively a respiratory gas flowing between a patient and an anaesthetic machine by means of the flow sensor, further comprising the step of collecting a time sequence of the pressure intensity x1, x2, x3 and x4 respectively corresponding to four consecutive sampling points of time within an arbitrary time interval and the flow value S corresponding to that time interval as the basis for the following judgment, as well as calculating three pressure difference variables using the equations dx1=x1−x2, dx2=x2−x3 and dx3=x3−x4;

c. judging that the flow sensor is reversedly connected and sending an alarm signal indicating the reverse connection of the flow sensor to a main controller when any one of the following two instances appears:

1) x1, x2 and x3 are all smaller than zero and meanwhile x1 and x3 are all equal to or greater than x2, and the flow value S is smaller than a predetermined first threshold value f1; and 2) dx1, dx2 and dx3 are all greater than zero and meanwhile dx1 and dx3 are smaller than or equal to dx2, and the flow value S is greater than a predetermined second threshold value f2.

The first threshold value f1 is set at −2 liters/minute and the second threshold value f2 is set at 3 liters/minute, both of which are used for eliminating the misjudgment caused by tiny and weak interference.

The invention claimed is:

1. A method for judging the reverse connection of a flow sensor in a respiratory mechanics measurement, comprising the following steps of:

a. connecting the flow sensor to a respiratory mechanics measuring module;

b. sampling consecutively airway pressures and flows of a respiratory gas flowing between a patient and an anaesthetic machine; and c. judging that the flow sensor is reversedly connected and sending an alarm signal indicating the reverse connection of the flow sensor to a main controller when any one of the following two instances appears:

c1) when the airway pressure decreases to the lowest point, the flow has a negative value while the patient is inhaling; and c2) around the time when the pressure intensity decreases the fastest, the flow has a positive value.

2. The method for judging the reverse connection of a flow sensor according to claim 1, wherein the step of sampling consecutively the airway pressures and flows of the respiratory gas flowing between the patient and the anesthetic machine comprises the following steps of: collecting a time sequence of the pressure intensity x1, x2, x3 and x4 respectively corresponding to four consecutive sampling points of time within an arbitrary time interval and a flow value S corresponding to that time interval as the basis for judgment, and calculating three pressure difference variables using the equations dx1=x1−x2, dx2=x2−x3 and dx3=x3−x4; and wherein the two instances, the occurrence of anyone of which indicates the reverse connection of the flow sensor, are as follows:

for step c1), x1, x2 and x3 are all smaller than zero and meanwhile x1 and x3 are equal to or greater than x2, and the flow value S is smaller than a predetermined first threshold value f1; and for step c2), dx1, dx2 and dx3 are all greater than zero and meanwhile dx1 and dx3 are smaller than or equal to dx2, and the flow value S is greater than a predetermined second threshold value f2.

3. The method for judging the reverse connection of a flow sensor according to claim 2, wherein the first threshold value f1 is set at −2 liters/minute and the second threshold value f2 is set at 3 liters/minute, both of which are used for eliminating misjudgment caused by tiny and weak interference.

4. A respiratory mechanics measuring module, comprising a flow sensor, a differential pressure sensor and a sampled signal processing circuit which are connected in series, the sampled signal processing circuit transferring calculation results to a main controller, and further comprising a flow sensor reverse connection judging module and an alarm, wherein the flow sensor reverse connection judging module judges whether the flow sensor is reversedly connected based on output signals of the differential pressure sensor, and the alarm sends a prompting signal indicating the flow sensor reverse connection to the main controller when the flow sensor reverse connection judging module judges that the flow sensor is reversedly connected.

5. The respiratory mechanics measuring module according to claim 4, wherein the sampled signal processing circuit comprises an amplification circuit connected to a signal output end of the differential pressure sensor, an analog-to-digital converter, a gain controller and a single chip processor which is in bi-directional communication with the analog-to-digital converter and the main controller, respectively.

6. The respiratory mechanics measuring module according to claim 5, wherein the flow sensor reverse connection judging module is an algorithm program solidified in the single chip processor.

7. A method for judging the reverse connection of a flow sensor in respiratory mechanics measurement, comprising the following steps of:
a. providing a respiratory mechanics measuring module and connecting thereto the flow sensor to be judged, the respiratory mechanics measuring module comprising a differential pressure sensor, a sampled signal processing circuit and an alarm;
b. measuring four pressure intensity values x1, x2, x3 and x4 of a respiratory gas in an airway corresponding to four consecutive sampling points of time within an arbitrary time interval and a flow value S of that time interval using the differential pressure sensor and the flow sensor, respectively, and calculating three pressure difference variables in the sampled signal processing circuit using the equations dx1=x1−x2, dx2=x2−x3 and dx3=x3−x4; and
c. sending an alarm signal indicating the reverse connection of the flow sensor with the alarm, if x1, x2 and x3 are all smaller than zero and meanwhile x1 and x3 are equal to or greater than x2, and the flow value S is smaller than a predetermined first threshold value f1; or if dx1, dx2 and dx3 are all greater than zero and meanwhile dx1 and dx3 are smaller than or equal to dx2, and the flow value S is greater than a predetermined second threshold value f2.

8. The method for judging the reverse connection of a flow sensor according to claim 7, wherein the sampled signal processing circuit comprises an amplification circuit connected to a signal output end of the differential pressure sensor, an analog-to-digital converter, a gain controller and a single chip processor.

9. The method for judging the reverse connection of a flow sensor according to claim 8, wherein an algorithm program used for judging the reverse connection of the flow sensor is solidified in the single chip processor.

* * * * *